United States Patent [19]

Bissett

[11] Patent Number: 5,739,156
[45] Date of Patent: Apr. 14, 1998

[54] METHODS OF USING 2,4-DIENOIC ACID ESTERS OF TOCOPHEROLS TO REDUCE FREE RADICAL DAMAGE IN MAMMALIAN CELLS

[75] Inventor: Donald Lynn Bissett, Hamilton, Ohio

[73] Assignee: The Procter & Gamble Company, Cincinnati, Ohio

[21] Appl. No.: 902,868

[22] Filed: Jul. 30, 1997

Related U.S. Application Data

[63] Continuation of Ser. No. 309,838, Sep. 21, 1994, abandoned.

[51] Int. Cl.$^6$ ............................................. A61K 31/355
[52] U.S. Cl. ............................................. 514/458
[58] Field of Search ................................. 514/458

[56] References Cited

U.S. PATENT DOCUMENTS

| | | | |
|---|---|---|---|
| 3,903,297 | 9/1975 | Robert | 424/305 |
| 3,989,816 | 11/1976 | Rhaadhyaksha | 424/60 |
| 4,017,641 | 4/1977 | DiGiulio | 424/365 |
| 4,130,667 | 12/1978 | Smith | 424/361 |
| 4,537,776 | 8/1985 | Cooper | 514/424 |
| 4,552,872 | 11/1985 | Cooper et al. | 514/175 |
| 4,557,934 | 12/1985 | Cooper | 424/128 |
| 4,847,071 | 7/1989 | Bissett et al. | 424/59 |
| 4,847,072 | 7/1989 | Bissett et al. | 424/59 |
| 4,954,487 | 9/1990 | Cooper et al. | 514/159 |

FOREIGN PATENT DOCUMENTS

| | | | |
|---|---|---|---|
| 0313305 | 4/1989 | European Pat. Off. | A61K 7/40 |
| WO91/16034 | 10/1991 | WIPO | A61K 7/42 |
| WO91/16035 | 10/1991 | WIPO | A61K 7/42 |

OTHER PUBLICATIONS

*Remington's Pharmasceutical Sciences*, 17 ed., Chapter 85, p. 1518 (1985).

Buettner et al., :"Ascorbate Free Radical as a Marker of Oxidative Stress: An EPR Study", *Free Radical Biology of Medicine*, vol. 14 pp. 49–55 (1993).

*Primary Examiner*—Kimberly Jordan
*Attorney, Agent, or Firm*—Loretta J. Henderson; Milton B. Graff, IV; John M. Howell

[57] ABSTRACT

The subject invention involves a method of reducing non-ultraviolet-induced free radical damage in mammals comprising administering to a mammal a composition comprising a safe and effective amount of a compound selected from 2,4-dienoic acid esters of tocopherols and mixtures of such compounds.

15 Claims, No Drawings

METHODS OF USING 2,4-DIENOIC ACID ESTERS OF TOCOPHEROLS TO REDUCE FREE RADICAL DAMAGE IN MAMMALIAN CELLS

This is a continuation of application Ser. No. 08/309,838, filed on Sep. 21, 1994, now abandoned.

The subject invention relates to the field of protecting mammals from free radical damage and conditions accelerated by free radical damage. Specifically, the subject invention relates to novel methods of using 2,4-dienoic acid esters of tocopherols for reducing the level of free radicals in mammalian cells.

BACKGROUND OF THE INVENTION

Free radicals, in particular oxygen radicals, in mammalian cells arise from a variety of environmental sources. Such sources include smoke, pollution and radiation in addition to normal cell metabolism and inflammatory processes. Free radicals are known to be damaging to biological tissue components such as structural proteins, membrane lipids and nucleic acids, resulting in alteration or loss of tissue and cell function, cell death, and cancer. A well recognized source for generation of tissue damaging radicals is radiation, such as UV radiation which causes high levels of radical production in the skin, leading to skin cancer and pre-mature skin aging (skin wrinkling). The use of tocopherol sorbate for preventing ultraviolet-induced damage to skin is disclosed in U.S. Pat. No. 4,847,072 issued to Bissett and Bush on Jul. 11, 1989.

Based on a growing body of evidence, it is believed that free radicals produced as by-products in normal metabolism can cause damage which is responsible for chronological aging of all tissues, including the skin. This has been termed the free radical theory of aging. Such free radicals are often produced by causes other than exposure of tissues to ultraviolet light.

The mammalian body has a variety of anti-radical defenses, such as small molecule anti-oxidants (e.g., vitamin C, vitamin E, beta-carotene) and anti-oxidant enzymes (e.g., superoxide dismutase, catalase). However, these defenses are often not sufficient to combat the levels or types of radicals produced from environmental or endogenous sources. Therefore, to more completely combat the damaging effects of free radicals, especially oxygen radicals, free radical scavengers and anti-oxidants can be used. These compounds react with the radical species to convert them to stable, non-reactive materials. It is an object of the subject invention to provide methods for reducing nonultraviolet-induced free radical damage in mammalian cells.

SUMMARY OF THE INVENTION

The subject invention involves a method of reducing nonultraviolet-induced free radical damage in mammalian cells comprising administering to a mammal a composition comprising a safe and effective amount of a compound selected from 2,4-dienoic acid esters of tocopherols, or a mixture of such compounds.

DETAILED DESCRIPTION OF THE INVENTION

It has been unexpectedly found that compositions comprising the subject compounds exhibit the ability to reduce levels of free radicals in mammalian tissues. This reduction of the levels of free radicals occurs in mammalian cells which have not experienced substantial recent exposure to ultraviolet light. Exposure to ultraviolet light is known to cause a high level of free radicals to form in mammalian cells. It has surprisingly been found that the subject compounds reduce the levels of free radicals in cells not recently exposed to ultraviolet light to a substantially greater extent than other anti-radical compounds.

While the subject invention is not limited to any particular mode of action, it is believed that the subject compounds may reduce the level of free radicals in mammalian cells by preventing the formation of the most damaging radical species. The subject compounds are believed to react efficiently with the above mentioned radical species. The subject compounds, which act as radical scavengers, are unexpectedly effective against both environmentally induced radical production as well as the endogenous radical production arising from metabolism. The subject compounds are also believed to reduce or prevent the depletion of the natural reserve of Vitamin C in mammalian cells.

As used herein, "alkyl" means a substituted or unsubstituted carbon-containing chain which may be straight or branched, saturated, monounsaturated (i.e., one double or triple bond in the chain), or polyunsaturated (i.e., two or more double bonds in the chain; two or more triple bonds in the chain; one or more double and one or more triple bonds in the chain).

As used herein, "topical application" means directly laying on or spreading on outer skin.

As used herein, "pharmaceutically-acceptable" means that salts, drugs, medicaments or inert ingredients which the term describes are suitable for use in contact with the tissues of humans and lower animals without undue toxicity, incompatibility, instability, irritation, allergic response, and the like, commensurate with a reasonable benefit/risk ratio.

As used herein, "safe and effective amount" means an amount of compound or composition sufficient to significantly induce a positive modification in the condition to be treated, but low enough to avoid serious side effects (at a reasonable benefit/risk ratio), within the scope of sound medical judgment. The safe and effective amount of the compound or composition will vary with the particular condition being treated, the age and physical condition of the patient being treated, the severity of the condition, the duration of the treatment, the nature of concurrent therapy, the specific compound or composition employed, the particular pharmaceutically-acceptable carrier utilized, and like factors within the knowledge and expertise of the attending physician.

As used herein, "free radical" means an atom or group of atoms that have one or more unpaired electrons. Such atoms or groups of atoms are highly reactive and unstable species. Also included among "free radicals" are other oxygen species which are highly reactive toward biological systems. Some "free radicals" are produced by the catalytic action of metals (e.g., iron or copper) or are more reactive toward biological systems in the presence of metals (e.g., iron or copper). Specific non-limiting examples of "free radicals" as defined above are:

| | |
|---|---|
| superoxide | $O_2^-$ |
| hydroperoxyl radical | $HO_2-$ |
| peroxide ion | $O_2^{2-}$ |
| hydroperoxyl anion | $HO_2^-$ |
| hydroxyl radical | $HO-$ |
| singlet oxygen | $^1O_2$ |

-continued

| | |
|---|---|
| hydrogen peroxide | $H_2O_2$ |
| ferryl iron | $FeO^{2+}$ |
| perferryl iron | $FeO_4^{3-}$ |

As used herein, "nonultraviolet-induced free radicals" means free radicals occurring in mammalian cells which are formed in such cells due to conditions other than exposure of the cells to ultraviolet light.

As used herein, "free radical damage" means the alteration in structure, function, composition, or other properties of biological tissues, organs, cells, or constituents that result from the effect of a free radical on them. Since free radicals are highly reactive and unstable species, they will in general react with a wide variety of biological targets to damage them. For example, the oxidation of lipids (lipid peroxidation), especially of cell membrane lipid, is a well-known damaging effect of radicals in biological systems.

Active Agent

The subject invention involves a method for protecting mammalian cells from nonultraviolet-induced free radical damage by reducing the level of free radicals in mammalian cells by administering to the mammal a safe and effective amount of a compound selected from 2,4-dienoic acid esters of tocopherols or a mixture of such compounds (mixed isomers).

As used herein, "tocopherols" include compounds having the following structure:

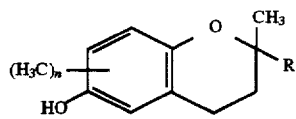

wherein n is an integer selected from 0, 1, 2 and 3; and R is

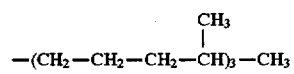

or

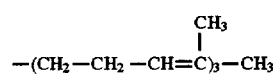

Preferred n is 2 or 3, especially 3.
Preferred R is

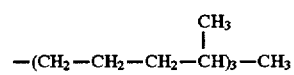

Preferred tocopherols which are subject compounds are naturally-occurring tocopherols including the following:

alpha-tocopherol (Vitamin E) having the structure:

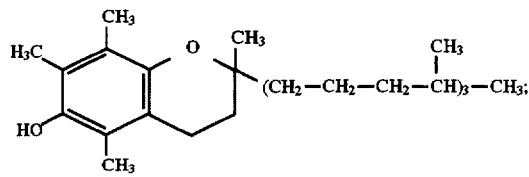

beta-tocopherol having the structure:

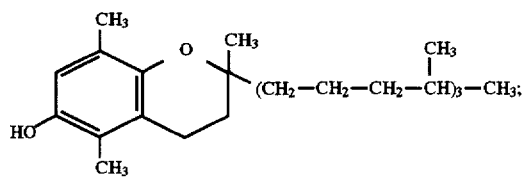

gamma-tocopherol having the structure:

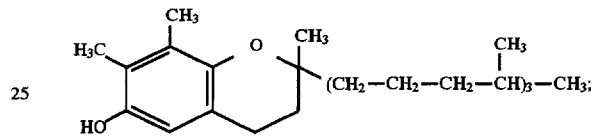

delta-tocopherol having the structure:

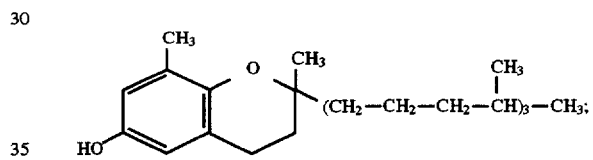

epsilon-tocopherol having the structure:

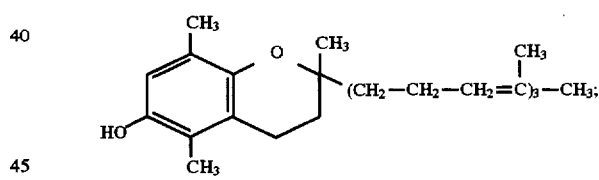

$zeta_1$-tocopherol having the structure:

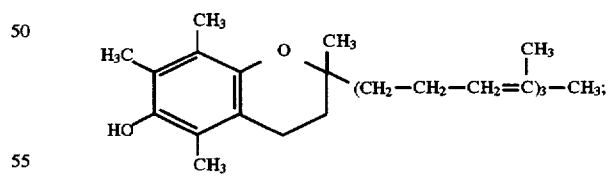

$zeta_2$-tocopherol having the structure:

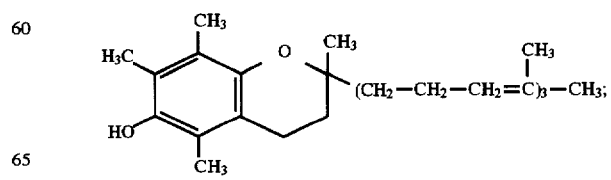

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of the invention.

eta-tocopherol having the structure:

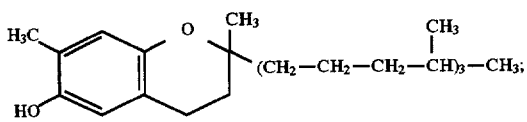

Tocopherols often occur naturally as mixtures of some or all of the above compounds.

Also preferred tocopherols which are part of the subject compounds are synthetic tocopherols.

Preferred synthetic tocopherols which are subject compounds include the following:
tocol having the structure:

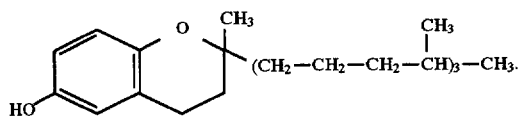

Other tocopherols shown above as naturally-occuring can also be made synthetically, especially alpha-tocopherol and delta-tocopherol.

As used herein, "2,4-dienoic acids" include compounds having the following structure:

wherein R' is hydrogen or alkyl having from 1 to about 7 carbon atoms. Preferred R' is unsubstituted. Preferred R' is saturated. Preferred R' is straight chain. Preferred R' is $C_1$–$C_3$ alkyl, especially methyl. Preferred R' is also $C_2$–$C_7$ alkyl, more preferred is $C_2$–$C_5$ alkyl, more preferred still is $C_2$–$C_3$ alkyl.

The most preferred 2,4-dienoic acid which is part of the subject compounds is sorbic acid:

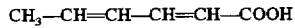

The subject invention compounds are esters where the above 2,4-dienoic acids are esterified with the hydroxy moiety at the 6-position of the benzopyran-6-ol ring of the above tocopherols.

Preferred active compounds of the subject invention include alpha-tocopherol sorbate, tocol sorbate, delta-tocopherol sorbate, and tocopherol (mixed isomers) sorbate. The most preferred compound of the subject invention is alpha-tocopherol sorbate.

Combination Actives

A. Sunscreens and Sunblocks

Reduction of the level of free radicals in mammalian cells can be achieved by using combinations of the subject compounds together with sunscreens or sunblocks. A known inducer of free radicals is ultraviolet radiation. Thus, in topical compositions, the inclusion of sunscreens/sunblocks would increase protection against radical production and subsequent damage. Useful sunblocks include, for example, zinc oxide and titanium dioxide. The combination of an active agent, with a UVA and/or UVB sunscreen is desirable. The inclusion of sunscreens in compositions useful in the subject invention at low levels does not greatly reduce the tanning response of the user but enhances the effectiveness of the subject compositions. A wide variety of conventional sunscreening agents are suitable for use in combination with a subject active agent. Sagarin, et al., at Chapter VIII, pages 189 et seq., of Cosmetics Science and Technology, disclose numerous suitable agents.

A safe and effective amount of sunscreen may be used in the compositions useful in the subject invention. The sunscreening agent must be compatible with the active agent. The composition preferably comprises from about 1% to about 20%, more preferably from about 2% to about 10% of a sunscreening agent. Exact amounts will vary depending upon the sunscreen chosen and the desired Sun Protection Factor.

B. Anti-Inflammatory Agents

In a preferred composition useful in the subject invention, an anti-inflammatory agent is included as an active along with a subject compound. The inclusion of an anti-inflammatory agent enhances the benefits of the compositions because the mammalian body will respond to radical damage by mounting an inflammation response which can lead to additional cell damage. The anti-inflammatory agent also protects strongly in the UVA radiation range (though it also provides some UVB protection as well). (See U.S. Pat. No. 4,847,071, Bissett, Bush, and Chatterjee, issued Jul. 11, 1989, incorporated herein by reference; and U.S. Pat. No. 4,847,069, Bissett and Chatterjee, issued Jul. 11, 1989, incorporated herein by reference.)

A safe and effective amount of an anti-inflammatory agent may be added to the compositions useful in the subject invention, preferably from about 0.1% to about 10%, more preferably from about 0.5% to about 5%, of the composition. The exact amount of anti-inflammatory agent to be used in the compositions will depend on the particular anti-inflammatory agent utilized since such agents vary widely in potency.

C. Chelators

In a preferred composition useful in the subject invention, a chelating agent is included as an active along with a subject compound. As used herein, "chelating agent" means an active agent capable of removing a metal ion from a system by forming a complex so that the metal ion cannot readily participate in or catalyze chemical reactions. The inclusion of a chelating agent increases the benefits of the composition.

A safe and effective amount of a chelating agent may be added to the is compositions useful in the subject invention, preferably from about 0.1% to about 10%, more preferably from about 1% to about 5%, of the composition. Chelators useful in compositions are disclosed in U.S. patent application Ser. No. 619,805, Bissett, Bush & Chatterjee, filed Nov. 27, 1990 (which is a continuation of U.S. patent application Ser. No. 251,910, filed Oct. 4, 1988); U.S. patent application Ser. No. 514,892, Bush & Bissett, filed Apr. 26, 1990; U.S. patent application Ser. No. 657,847, Bush, Bissett & Chatterjee, filed Feb. 25, 1991; and U.S. patent application Ser. No. 776,506, Bush, filed Oct. 11, 1991; all incorporated herein by reference. The additional chelators preferred include:

kojic acid
2,3-bis-(2-pyridyl)-pyrazine
3-(4-phenyl-2-pyridyl)-5-phenyl-1,2,4-triazine
2,3-bis-(2-pyridyl)-5,6-dihydropyrazine
2,4,6-tri-(2-pyridyl)-1,3,5-triazine
1-pyrrolidine carbodithioic acid
di-2-pyridyl ketone
phenyl 2-pyridyl ketoxime 2,3-dihydroxy naphthalene
2,3-dihydroxy pyridine
3-hydroxy-2-methyl-4-pyrone
2,3-dihydroxy benzoic acid
ethylenediamine-N,N-bis-(2-hydroxy-phenylacetic acid) dimethyl ester
2-furildioxime
2-furilmonoxime
1-phenyl-1,2-propanedione-2-oxime
1-phenyl-1,3-butanedione
1-hydroxy-4-methyl-t-(2,4,4-trimethyl-pentyl)-2(1H)-pyridinone
diethyldithiocarbamic acid
deferoxamine
1,2-dimethyl-3-hydroxypyrid-4-one In a preferred composition useful in the subject invention, compositions comprise one, any two, or all three of a sunscreening agent, anti-inflammatory agent, and/or chelating agent included as actives along with the subject active agent. The inclusion of two, or all three of these agents with the active agent increases the benefits of the composition.

Methods for Reducing Free Radical Damage in Mammalian Cells

The subject invention relates to methods for reducing the level of free radicals in mammalian cells. The reduction of the level of free radicals in mammalian cells reduces the level of free radical aging in the cells.

The level of free radicals in mammalian cells can be determined experimentally using radical traps. Methods for EPR (electron paramagnetic resonance) analysis of radicals in the skin include the following:

Female albino Skh:HR-1 hairless mice are treated topically 3 times per week (e.g., Monday, Wednesday, and Friday) on the dorsal skin surface with 0.1 ml of test material in isopropanol or with isopropanol alone. The skin is then analyzed in vitro in an EPR instrument (Bruker ESP 300 spectrometer, Bruker Instruments, Karlsruhe, Germany) for level of radicals using two radical traps: (1) endogenous ascorbate in which the skin's endogenous ascorbic acid serves as the trap and ascorbyl radical is detected; and (2) exogenous POBN (alpha-(4-pyridyl-1-oxide)-N-tertbutyl nitrone) in which 0.05 ml of 250 mM POBN is applied to the skin sample surface for 10 minutes prior to analysis in the EPR. The skin samples are then placed in a tissue cell (Wilmad Glass Co., Buena, N.J.) and positioned in the EPR cavity.

The above ascorbyl radical method is non-specific in that a wide range of radicals generated in the skin are trapped by ascorbate. This method is described in the following reference: Buettner, G. R., and B. A. Jurkiewicz, "Ascorbate Free Radical as a Marker of Oxidative Stress: An EPR Study", *Free Radical Biology & Medicine*, Vol. 14 (1993), pp. 49–55.

The above POBN method captures a carbon-centered lipid radical and thus more specifically traps lipid oxidation radicals. The measurement is made at room temperature using the EPR instrument. The POBN radical adduct gives a triplet of doublets signal. Only the first doublet signal height is measured for each experiment; there is no interference from other signals for this first doublet. The EPR settings are: microwave power, 40 milliwatts; modulation amplitude, 0.75 G; time constant, 0.3 sec; scan rate, 60 G/41.9 sec; receiver gain, $1 \times 10^6$.

The subject methods for reducing nonultraviolet-induced free radical damage in mammalian cells involve administration of a safe and effective amount of a subject compound. The amount of compound administered and frequency of administration will vary widely depending upon the conditions of the cells already in existence in the subject and the level of treatment desired.

The preferred modes of administration are topically, orally, and parenterally (for example, by subcutaneous injection, intramuscular injection, intra-articular injection, intravenous injection and the like). Thus, specific modes of administration include, without limitation, peroral, transdermal, mucosal, sublingual, intramuscular, intravenous, intraperitoneal, and subcutaneous administration, as well as topical application.

Various oral dosage forms are useful for the methods of the subject invention including such solid forms as tablets, capsules, granules, bulk powders and microcapsules of the subject compounds. These oral dosage forms comprise a safe and effective amount, usually at least about 5%, and preferably from about 10% to about 50% of the compound of the subject invention. Tablets can be compressed, enteric-coated, sugar-coated or filmcoated containing suitable binders, lubricants, surfactants, diluents, disintegrating agents, coloring agents, flavoring agents, preservatives, flow-inducing agents, and melting agents. Liquid oral dosage forms include aqueous and nonaqueous solutions, emulsions, suspensions, solutions and/or suspensions reconstituted from non-effervescent granules, containing suitable solvents, preservatives, emulsifying agents, suspending agents, diluents, sweeteners, melting agents, coloring agents, and flavoring agents. Liquid oral dosage forms may be encapsulated in a solid shell, and thus be administered like a solid capsule. Preferred carriers for oral administration include gelatin and propylene glycol. Specific examples of pharmaceutically-acceptable carriers and excipients that may be used in formulating oral dosage forms containing compounds of the subject invention are described in U.S. Pat. No. 3,903,297, Robert, issued Sep. 2, 1975, incorporated by reference herein. Techniques and compositions for making solid oral dosage forms are described in Marshall, "Solid Oral Dosage Forms," *Modern Pharmaceutics*, Vol. 7, (Banker and Rhodes, editors), 359–427 (1979), incorporated herein by reference. Techniques and compositions for making tablets (compressed, formulas and molded), capsules (hard and soft gelatin) and pills are described in *Remington's Pharmaceutical Sciences* (Arthur Osol, editor), 1553–1593 (1980), incorporated herein by reference.

The preferred unit dosage form for oral administration is tablets, capsules, encapsulated liquids, and the like, comprising a safe and effective amount of a compound of the subject invention. Preferably oral dose forms comprise from about 0.001 g to about 5g of a compound of the subject invention, more preferably from about 0.01 g to about 2g and most preferably from about 0.1g to about 1 g, for a 50–70 kg person.

Oral administration can be used to reduce the level of free radicals through oral dosing of a pharmaceutical composition comprised of a safe and effective amount of the compound of the subject invention in a suitable oral pharmaceutical carrier. The compound is absorbed by the gastrointestinal tract. The pharmaceutical composition may consist of solid dosage forms such as tablets, hard gelatin capsules, soft gelatin capsules, bulk powders, and microcapsules of the drug. Alternately, it may consist of a liquid dosage form such as an aqueous or nonaqueous solution, emulsion, or suspension.

The amount of the compound ingested depends upon the bioavailability of the compound from the oral pharmaceutical composition. Typically, however, the compounds of the subject invention are dosed in an amount of from about 0.001 mg/kg of body weight to about 100 mg/kg, preferably from about 0.01 to about 50 mg/kg of body weight, more preferably from about 0.1 to about 20 mg/kg of body weight, also preferably from about 1 mg to about 10 mg/kg of body weight. The amount of the pharmaceutical composition depends upon the percent of compound within its formula, which is a function of the amount of the compound required per dose, its stability, release characteristics and other pharmaceutical parameters. Generally, the oral pharmaceutical composition will comprise from about 5% to about 50% of the compound of the subject invention.

Oral application preferably ranges from about weekly to about 5 times daily, more preferably from about twice a week to about four times daily, more preferably still from about every other day to about 3 times daily, also preferably from about once a day to about twice a day. Treatment is continued for at least 7 days, more preferably 6 months, even more preferably 1 year, more preferably still 5 years, also preferably 10 years.

Compositions of the subject invention are preferably administered topically to a mammal by the direct laying on or spreading of the composition on the skin. Topical compositions comprising tocopherol sorbate are disclosed in U.S. Pat. No. 4,847,072 issued to Bissett and Bush Jul. 11, 1989, which is hereby incorporated herein by reference. Other compounds of the subject invention can be substituted for tocopherol sorbate in such compositions.

The topical compositions useful in the subject invention involve compositions suitable for topical application to mammalian skin, the composition comprising a safe and effective amount of an active compound or mixture of such actives as described hereinabove, and a pharmaceutically-acceptable topical carrier. The subject compositions preferably contain from about 0.001% to about 20%, more preferably from about 0.01% to about 15%, more preferably still from about 0.1% to about 10%, also preferably from about 0.5% to about 2%, also preferably from about 1% to about 5%.

The topical compositions useful in the subject invention may be made into a wide variety of product types. These include, but are not limited to lotions, creams, beach oils, gels, sticks, sprays, ointments, pastes, mousses, cosmetics, shampoos, cream rinses, hair tonics and hair conditioners. These product types may comprise several types of carrier systems including, but not limited to solutions, emulsions, gels, solids, and liposomes. Topical compositions preferably comprise from about 1% to about 50%, more preferably from about 5% to about 25% of an emollient.

The topical compositions useful in the subject invention may include a safe and effective amount of penetration enhancing agent. A preferred amount of penetration enhancing agent is from about 1% to about 5% of the composition. Examples of useful penetration enhancers, among others, are disclosed in U.S. Pat. Nos. 4,537,776, Cooper, issued Aug. 27, 1985; 4,552,872, Cooper et al., issued Nov. 12, 1985; 4,557,934, Cooper, issued Dec. 10, 1985; 4,130,667, Smith, issued Dec. 19, 1978; 3,989,816, Rhaadhyaksha, issued Nov. 2, 1976; 4,017,641, DiGiulio, issued Apr. 12, 1977; and 4,954,487, Cooper, Loomans & Wickett, issued Sep. 4, 1990.

Other skin care product additives may also be included in the compositions useful in the subject invention. For example, collagen, hyaluronic acid, salicylic acid, phytic acid, hydroxyquinone, arbutin compounds, elastin, hydrolysates, primrose oil, jojoba oil, epidermal growth factor, soybean saponins, mucopolysaccharides, and mixtures thereof may be used.

Various vitamins may also be included in the compositions useful in the subject invention. For example, vitamin A, and derivatives thereof, vitamin $B_2$, biotin, pantothenic acid, vitamin D, and mixtures thereof may be used.

A safe and effective amount of active agent, in a topical composition, is applied, generally from about 0.001 mg to about 2 mg per $cm^2$ skin per application, preferably from about 0.005 mg to about 1 mg per $cm^2$ skin per application, more preferably from about 0.01 mg to about 0.5 mg/$cm^2$, also preferably from about 0.02 mg to about 0.2 mg/$cm^2$. Application preferably ranges from about weekly to about 5 times daily, more preferably from about twice a week to about four times daily, more preferably still from about every other day to about 3 times daily, also preferably from about once a day to about twice a day. The subject compositions are preferably applied to an area of from about 10 $cm^2$ to about 10,000 $cm^2$ skin for each application, more preferably from about 100 $cm^2$ to about 5,000 $cm^2$ skin, also preferably from about 500 $cm^2$ to about 1000 $cm^2$ skin. Treatment is continued for at least 7 days, more preferably 6 months, even more preferably 1 year, more preferably still 5 years, also preferably 10 years.

A preferred method of the subject invention involves applying both a safe and effective amount of a subject compound and a safe and effective amount of one or more of a sunscreening agent, an anti-inflammatory agent, and/or a chelating agent, to the skin simultaneously. As used herein, "simultaneous application" or "simultaneously" means applying the agents to the skin at the same situs on the body at about the same time. Though this can be accomplished by applying the agents separately to the skin, preferably a composition comprising all the desired agents commingled is applied to the skin. The amount of sunscreening agent applied is preferably from about 0.05 mg to about 0.5 mg per $cm^2$ skin. The amount of anti-inflammatory agent applied is preferably from about 0.005 mg to about 0.5 mg, more preferably from about 0.01 mg to about 0.1 mg per $cm^2$ skin. The amount of chelating agent preferably applied is from about 0.001 mg to about 1.0 mg, more preferably from about 0.01 mg to about 0.5 mg, still more preferably from about 0.05 mg to about 0.1 mg per $cm^2$ skin. The amount of the active compound of the subject invention applied is preferably from about 0.001 mg to about 2 mg per $cm^2$ skin per application, more preferably from about 0.01 mg to about 0.5 mg per $cm^2$ skin per application.

The compounds of the subject invention are also useful when injected. The dosage of the compound of the subject invention which is both safe and effective will vary with the particular condition being treated, the severity of the condition, the duration of treatment, the specific compound employed and its usage concentration, and like factors within the specific knowledge and expertise of the attending physician and commensurate with a reasonable benefit/risk ratio associated with the use of any drug compound. The injectable dosages and dosage ranges given herein are based on delivery of the compound of the subject invention to a 70 kg human and can be adjusted to provide equivalent dosages for patients of different body weights.

Methods and materials for manufacturing injectables can be found in *Remington's Pharmaceutical Sciences*, 17ed., 1985, Chapter 85, p. 1518, the disclosures of which are incorporated herein by reference in their entirety. The injectable dosage forms typically contain from about 0.001 mg/ml to about 100 mg/ml, preferably from about 0.01 mg/ml to about 10 mg/ml, more preferably from about 0.1 mg/ml to about 3.0 mg/ml, of the compound of the subject invention. The injectable dosage forms are typically administered from about once a week to about four times daily, more preferably from about twice a week to about three times daily, more preferably still, about three times a week to about twice daily, also preferably about once daily. Typically, from about 1 ml to about 100 mls of the composition are injected, preferably from about 10 mls to about 50 mls, more preferably about 25 mls.

In addition to the active compound as described hereinbefore, the pharmaceutical compositions useful in the present invention essentially comprise a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the pharmaceutical compositions are capable of being commingled with the compound of the present invention, and with each other, in a manner such that there is no interaction which would substantially reduce the pharmaceutical efficacy of the pharmaceutical composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers are sugars such as lactose, glucose and sucrose; starches such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils such a peanut oil, cottonseed oil, sesame oil, olive oil, corn oil and oil of theobroma; polyols such as propylene glycol, glycerine, sorbitol, mannitol, and polyethylene glycol; sugar; alginic acid; pyrogen-free water; isotonic saline; phosphate buffer solutions; cocoa butter (suppository base); emulsifiers, such as the Tweens®; as well as other non-toxic compatible substances used in pharmaceutical formulations. Wetting agents and lubricants such as sodium lauryl sulfate, as well as coloring agents, flavoring agents, excipients, tableting agents, stabilizers, antioxidants, and preservatives, can also be present.

The choice of a pharmaceutically-acceptable carrier to be used in conjunction with the compounds of the present invention is determined by the way the compound is to be administered. The preferred modes of administering the compounds of the present invention are orally, topically and by injection. Suitable pharmaceutically-acceptable carriers for topical application include those suited for use in creams, gels, tapes and the like; and for oral administration include those suited for tablets and capsules.

The pharmaceutically-acceptable carrier employed in conjunction with the compounds of the present invention is used at a concentration sufficient to provide a practical size to dosage relationship. The pharmaceutically-acceptable carriers, in total, may comprise from about 10% to about 99.9% by weight of the pharmaceutical compositions of the present invention, preferably from about 50% to about 99.5%, more preferably from about 80% to about 99%, also preferably from about 90% to about 95%, also preferably from about 95% to about 98%.

Pharmaceutically-acceptable carriers suitable for the preparation of unit dosage forms for oral administration and injection, and dosage forms for topical application are well-known in the art. Their selection will depend on secondary considerations like taste, cost, and/or shelf stability, which are not critical for the purposes of the subject invention, and can be made without difficulty by a person skilled in the art. Pharmaceutically-acceptable carriers useful in the compositions of the subject invention are described more fully hereinafter.

EXAMPLES

The following examples further describe and demonstrate embodiments within the scope of the subject invention. The examples are given solely for the so purpose of illustration and are not to be construed as limitations of the subject invention, as many variations thereof are possible without departing from the spirit and scope of the invention.

Example 1

A composition for oral administration is prepared by combining the following:

| Component | |
|---|---|
| Alpha-tocopherol sorbate | 1 kg |
| Sesame oil | to 4 liters |

The alpha-tocopherol sorbate is suspended in the sesame oil with the aid of sonication and is packaged in soft gelatin capsules using methods known in the art. Two of the resulting capsules, each containing 250 mg of the active, are administered to a 60 kg human, daily for a period of 4 years.

Example 2

A composition for oral administration is prepared by combining the following:

| Component | |
|---|---|
| Beta-tocopherol 2,4-octadienoate | 250 g |
| Propylene glycol | 1800 ml |
| Ethyl alcohol | 175 ml |
| Distilled water | 75 ml |
| Artificial cherry flavor | 10 ml |
| FD&C Red #40 | 0.2 g |

The above ingredients are combined to produce a syrup and are packaged under sterile conditions in 6 oz. bottles. One teaspoon of this formulation is administered to a 70 kg human, weekly for a period of one year.

Example 3

Tablets are prepared by conventional methods, such as mixing and direct compaction, formulated as follows:

| Component | mg per tablet |
|---|---|
| Tocol 2,4-pentadienoate | 500 |
| Microcrystalline cellulose | 400 |
| Sodium starch glycolate | 60 |
| Magnesium stearates | 10 |

One tablet is administered orally to a human daily for a period of one year or more.

Example 4

A topical composition is prepared by combining the following components utilizing conventional mixing techniques.

| Component | % Weight |
| --- | --- |
| Isopropanol | 98 |
| Alpha-tocopherol sorbate | 2 |

In a suitable vessel, the alpha-tocopherol sorbate is dissolved in the isopropanol with stirring. Use of an amount of the composition to deposit about 0.02 mg/cm$^2$ of the alpha-tocopherol sorbate to about 200 cm$^2$ of skin is appropriate. The composition is applied twice daily, for a period of five years.

Example 5

A topical composition is prepared by combining the following components utilizing conventional mixing techniques.

| Component | % Weight |
| --- | --- |
| Ethanol | 99.5 |
| Tocol sorbate | 0.5 |

In a suitable vessel, the tocol sorbate is dissolved in the ethanol with stirring. Use of an amount of the composition to deposit about 0.001 mg/cm$^2$ of the tocol sorbate to the skin is appropriate. The composition is applied four times daily over a 1000 cm$^2$ area of skin for a period of six months.

Example 6

A topical composition is prepared by combining the following components utilizing conventional mixing techniques.

| Component | % Weight |
| --- | --- |
| Ethanol | 49.00 |
| Propylene glycol | 25.00 |
| Deionized water | 25.00 |
| Tocopherol (mixed isomers) sorbate | 1.00 |

In a suitable vessel, the tocopherol sorbate is dissolved in the ethanol with stirring. Propylene glycol and deionized water are added with stirring. Use of an amount of the composition to deposit about 0.02 mg/cm$^2$ of the gamma-tocopherol 2,4-octadienoate to 2000 cm$^2$ of skin is appropriate. The composition is applied once a week for one year.

Example 7

A nonionic oil-in-water emulsion is prepared by combining the following components utilizing conventional mixing techniques:

| Component | % Weight |
| --- | --- |
| Deionized water | 78.73 |
| Propylene glycol | 3.00 |
| Octyl methoxycinnamate | 7.50 |
| Cetyl alcohol | 2.50 |
| Stearyl alcohol | 2.50 |
| Laureth 23 | 2.00 |
| C$_{12-15}$ alcohols benzoate | 2.00 |
| EDTA | 0.37 |
| Methylparaben | 0.20 |

-continued

| Component | % Weight |
| --- | --- |
| Propylparaben | 0.10 |
| Delta-tocopherol sorbate | 1.10 |

Use of an amount of the composition sufficient to deposit about 0.004 mg/cm$^2$ skin of the delta-tocopherol sorbate is appropriate. The composition is applied twice a week to about 500 cm$^2$ of skin for two years.

Example 8

A nonionic oil-in-water emulsion is prepared by combining the following components utilizing conventional mixing techniques:

| Component | % Weight |
| --- | --- |
| Deionized water | 78.73 |
| Propylene glycol | 3.00 |
| Octyl methoxycinnamate | 7.50 |
| Cetyl alcohol | 2.50 |
| Stearyl alcohol | 2.50 |
| Laureth 23 | 2.00 |
| C$_{12-15}$ alcohols benzoate | 2.00 |
| EDTA | 0.37 |
| Methylparaben | 0.20 |
| Propylparaben | 0.10 |
| Alpha-tocopherol sorbate | 1.10 |

Use of an amount of the composition sufficient to deposit about 0.05 mg/cm$^2$ of the alpha-tocopherol sorbate to about 100 cm$^2$ of skin is appropriate. The composition is applied once daily, for three years.

Example 9

An oil-in-water emulsion is prepared by combining the following components utilizing conventional mixing techniques.

| Component | % Weight |
| --- | --- |
| Deionized water | 78.05 |
| Permulon TR-2 (C10–C30 acrylate copolymer, B. F. Goodrich) | 0.30 |
| Distearyl dimethyl ammonium chloride | 0.15 |
| Tocol sorbate | 1.00 |
| 4-N,N-(2-ethylhexyl)methylaminobenzoic acid 4-ester of 2-hydroxy-4-(2-hydroxyethoxy)-benzophenone | 4.00 |
| 4-N,N-(2-ethylhexyl)methylaminobenzoic acid ester of 4-(2-hydroxyethoxy)dibenzoylmethane | 2.00 |
| Dimethyl isosorbide | 6.00 |
| Dioctyl malate | 6.00 |
| Cetyl alcohol | 1.00 |
| Stearyl alcohol | 1.00 |
| 99% triethanolamine | 0.50 |

Use of an amount of the composition sufficient to deposit about 0.1 mg/cm$^2$ of the tocol sorbate to about 1000 cm$^2$ of skin is appropriate. The composition is applied twice daily, for one year.

Example 10

A sunscreen composition is prepared by combining the following components utilizing conventional mixing techniques.

| Component | % Weight |
|---|---|
| Polypropylene glycol 15 stearyl ether | 15.00 |
| Sorbitan oleate | 2.00 |
| Octyl methoxy cinnamate | 7.50 |
| 2-furildioxime | 0.50 |
| Tocopherol (mixed isomers) sorbate | 1.00 |
| Propyl paraben | 0.15 |
| Butylated hydroxy toluene | 0.05 |
| Cyclomethicone | 20.00 |
| Sesame oil | 5.00 |
| Mineral oil (Blandol) | 48.8 |

Use of an amount of the composition is sufficient to deposit about 0.1 mg/cm2 of the tocopherol sorbate to the skin is appropriate. This composition is applied three times daily, for six months.

Example 11

A topical composition is prepared by combining the following components using conventional mixing techniques.

| Component | Weight % |
|---|---|
| Water | 69.363 |
| Tetrasodium EDTA | 0.020 |
| Glycerine | 3.000 |
| Triethanolamine | 0.100 |
| Fluid AP | 6.000 |
| Parsol 1789 | 3.000 |
| Parsol MCX | 7.500 |
| Ganex V220 | 0.500 |
| Stearly alcohol | 1.000 |
| Cetyl alcohol | 1.000 |
| Brij 721 | 0.531 |
| Brij 72 | 0.286 |
| Dimethicone gum | 0.500 |
| Salicylic acid | 2.000 |
| Salcare SC-95 | 2.000 |
| Alpha-tocopherol sorbate | 1.000 |
| Oxybenzone | 1.000 |
| Silicone DC 1403 | 1.000 |
| Fragrance | 0.200 |

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of the invention.

What is claimed is:

1. A method of reducing nonultraviolet-induced free radical damage in cells of living mammals comprising administering to a mammal a composition comprising a safe and effective amount of a compound selected from 2,4-dienoic acid esters of tocopherols and mixtures of such compounds.

2. The method of claim 1 wherein the 2,4-dienoic acid esters of tocopherols have the following structure:

$$R'-CH=CH-CH=CH-C(=O)-O-\text{[chroman ring with }(H_3C)_n\text{, O, }CH_3\text{, R]}$$

wherein:

(a) n is an integer from 0 to 3;

(b) R is 
$$-(CH_2-CH_2-CH_2-\underset{\underset{CH_3}{|}}{CH})_3-CH_3$$

or $$-(CH_2-CH_2-CH=\underset{\underset{CH_3}{|}}{C})_3-CH_3$$

and (c) R' is hydrogen or alkyl having from 1 to about 7 carbon atoms.

3. The method of claim 2 wherein R' is saturated and unsubstituted.

4. The method of claim 3 wherein R' is straight chain.

5. The method of claim 4 wherein R' is $C_1$–$C_3$ alkyl.

6. The method of claim 5 wherein R' is methyl.

7. The method of claim 2 wherein R' is hydrogen.

8. The method of claim 4 wherein R' is $C_2$–$C_7$ alkyl.

9. The method of claim 8 wherein R' is ethyl or n-propyl.

10. The method of claim 2, 6, 7 or 8 wherein the tocopherols are selected from the group consisting of alpha-tocopherol, beta-tocopherol, gamma tocopherol, delta-tocopherol, epsilon-tocopherol, $zeta_2$-tocopherol, $zeta_1$-tocopherol, eta-tocopherol, and mixtures thereof.

11. The method of claim 2, 6, 7 or 8 wherein the tocopherols comprise alpha-tocopherol.

12. The method of claim 2, wherein the tocopherols comprise delta-tocopherol.

13. The method of claim 2, wherein the tocopherols comprise tocol.

14. The method of claim 2 or 6 wherein the composition is administered to a human in a peroral dose form wherein from about 0.1 mg to about 20 mg of the compound is administered per kg of body weight, from about twice a week to about four times daily, for a period of one week or more.

15. The method of claim 2, 6, 7 or 8 wherein the composition is applied topically to the skin of a human wherein the amount of the compound applied to the skin is from about 0.01 mg to about 0.5 mg per cm² skin, from about twice a week to about four times a day, for a period of one week or more.

* * * * *